(12) United States Patent
Jin et al.

(10) Patent No.: US 9,943,290 B2
(45) Date of Patent: Apr. 17, 2018

(54) ULTRASOUND PROBE AND COMMUNICATION METHOD THEREOF

(71) Applicant: SAMSUNG MEDISON CO., LTD., Gangwon-do (KR)

(72) Inventors: Gil-ju Jin, Gangwon-do (KR); Mi-Jeoung Ahn, Gangwon-do (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 1146 days.

(21) Appl. No.: 14/080,528

(22) Filed: Nov. 14, 2013

(65) Prior Publication Data

US 2014/0323869 A1 Oct. 30, 2014

(30) Foreign Application Priority Data

Apr. 30, 2013 (KR) ........................ 10-2013-0048517

(51) Int. Cl.
*A61B 8/14* (2006.01)
*A61B 8/00* (2006.01)
*G06F 19/00* (2018.01)

(52) U.S. Cl.
CPC ............ *A61B 8/565* (2013.01); *A61B 8/4472* (2013.01); *A61B 8/465* (2013.01); *A61B 8/56* (2013.01);
(Continued)

(58) Field of Classification Search
CPC ..... A61B 8/4438; A61B 8/4472; A61B 8/465; A61B 8/56; A61B 8/565; G06F 19/327; G06F 19/3418
See application file for complete search history.

(56) References Cited

U.S. PATENT DOCUMENTS

2008/0228045 A1 9/2008 Gao et al.
2009/0043199 A1 2/2009 Pelissier et al.
(Continued)

FOREIGN PATENT DOCUMENTS

DE 102010018546 A1 11/2011
JP 2012-139491 A 7/2012
WO 2011-156815 A1 12/2011

OTHER PUBLICATIONS

Extended European Search Report dated Jul. 7, 2016 issued in European Patent Application No. 16156683.1.
(Continued)

*Primary Examiner* — Mark Remaly
(74) *Attorney, Agent, or Firm* — McDermott Will & Emery LLP (57) ABSTRACT

Provided are an ultrasound probe and a communication method of the ultrasound probe capable of selecting an ultrasound diagnosis apparatus and/or a wireless communication method that are most appropriate in an environment in which a plurality of ultrasound diagnosis apparatuses exist. A method of communicating with an ultrasound diagnosis apparatus, performed by the ultrasound probe, includes operations of obtaining a plurality of pieces of information about ultrasound diagnosis apparatuses; displaying an ultrasound diagnosis apparatus list, based on the plurality of pieces of information about the ultrasound diagnosis apparatuses; receiving an input for selecting an ultrasound diagnosis apparatus from the ultrasound diagnosis apparatus list; and wirelessly transmitting ultrasound image data to the ultrasound diagnosis apparatus, wherein the ultrasound image data is generated by the ultrasound probe.

9 Claims, 9 Drawing Sheets

(52) U.S. Cl.
CPC ........ *G06F 19/327* (2013.01); *G06F 19/3418* (2013.01); *A61B 8/4438* (2013.01)

(56)  References Cited

U.S. PATENT DOCUMENTS

| | | | |
|---|---|---|---|
| 2009/0057190 A1* | 3/2009 | Schmeisser | G06F 1/1632 206/592 |
| 2010/0036253 A1* | 2/2010 | Vezina | A61B 5/02028 600/453 |
| 2010/0160784 A1 | 6/2010 | Poland et al. | |
| 2010/0168576 A1 | 7/2010 | Poland et al. | |
| 2011/0105904 A1* | 5/2011 | Watanabe | A61B 8/00 600/443 |

OTHER PUBLICATIONS

Extended European Search Report issued in Application No. 13189196.2-1660 dated May 12, 2014.

* cited by examiner

ULTRASOUND PROBE AND COMMUNICATION METHOD THEREOF

CROSS-REFERENCE TO RELATED PATENT APPLICATION

This application claims the benefit of Korean Patent Application No. 10-2013-0048517, filed on Apr. 30, 2013, in the Korean Intellectual Property Office, the disclosure of which is incorporated herein in its entirety by reference.

BACKGROUND OF THE INVENTION

1. Field of the Invention

The present invention relates to an ultrasound probe and a communication method thereof, and more particularly, to a wireless ultrasound probe that wirelessly communicates with an ultrasound diagnosis apparatus, and a communication method of the wireless ultrasound probe.

2. Description of the Related Art

An ultrasound system delivers an ultrasound signal, which is generated at a transducer of an ultrasound probe, to a predetermined internal part of a target object, and obtains an image of the internal part of the target object by receiving information of an echo signal reflected from the internal part of the target object. In particular, the ultrasound system is used for medical purposes including observation, detection of foreign materials, damage measurement, or the like that are related to the internal part of the target object.

Compared to a diagnosis apparatus using X-rays, the ultrasound system is stable, displays an image in real-time, and is safe without a risk of radioactivity, and thus, the ultrasound system is widely used with an image diagnosis apparatus.

Here, when a user obtains the image of the target object by using the ultrasound probe, inconvenience is experienced due to a communication cable that connects the ultrasound probe and an ultrasound diagnosis apparatus. In order to improve operability of the ultrasound probe by solving this inconvenience, it is required to arrange a wireless ultrasound probe that connects to the ultrasound diagnosis apparatus via wireless communication.

However, when one ultrasound probe is subordinate to one ultrasound diagnosis apparatus, respective ultrasound probes have to be arranged to correspond to respective ultrasound diagnosis apparatuses, such that it is expensive to arrange the ultrasound probes and it is difficult to control the ultrasound probes.

Thus, it is required to arrange a wireless ultrasound probe that is not subordinate to one ultrasound diagnosis apparatus and that is capable of communicating with a plurality of ultrasound diagnosis apparatuses. Also, in a case of an ultrasound system capable of providing an ultrasound image in real-time to a user, it is required to stably drive the wireless ultrasound probe that transmits data of the ultrasound image. Thus, in order to stably drive the wireless ultrasound probe, it is required to select an ultrasound diagnosis apparatus and/or a wireless communication method that are most appropriate in an environment in which a plurality of ultrasound diagnosis apparatuses exist.

SUMMARY OF THE INVENTION

The present invention provides a wireless ultrasound probe capable of communicating with a plurality of ultrasound diagnosis apparatuses, and a communication method of the wireless ultrasound probe.

The present invention also provides a wireless ultrasound probe capable of efficiently delivering user-required information by displaying an ultrasound diagnosis apparatus list, based on a plurality of pieces of information about ultrasound diagnosis apparatuses, and a communication method of the wireless ultrasound probe.

According to an aspect of the present invention, there is provided a method, performed by an ultrasound probe, of communicating with an ultrasound diagnosis apparatus, the method including operations of obtaining a plurality of pieces of information about ultrasound diagnosis apparatuses; displaying an ultrasound diagnosis apparatus list, based on the plurality of pieces of information about the ultrasound diagnosis apparatuses; receiving an input for selecting an ultrasound diagnosis apparatus from the ultrasound diagnosis apparatus list; and wireless transmitting ultrasound image data to the ultrasound diagnosis apparatus, wherein the ultrasound image data is generated by the ultrasound probe.

The ultrasound diagnosis apparatus list may include information about a wireless communication method that can be used by the ultrasound probe to transmit the ultrasound image data to at least one of the ultrasound diagnosis apparatuses. The operation of wireless transmitting the ultrasound image data may include operations of determining a wireless communication method that is used to transmit the ultrasound image data to the ultrasound diagnosis apparatus; and transmitting the ultrasound image data to the ultrasound diagnosis apparatus by using the wireless communication method. Here, the wireless communication method may include at least one of wireless local area network (LAN), Wi-Fi, Bluetooth, ZigBee, Wi-Fi Direct (WFD), ultra wideband (UWB), infrared data association (IrDA), Bluetooth low energy (BLE), near field communication (NFC), wireless broadband internet (Wibro), world interoperability for microwave access (WiMAX), shared wireless access protocol (SWAP), and radio frequency (RF) communication.

The plurality of pieces of information about the ultrasound diagnosis apparatuses may include information about a diagnosis department or a diagnosis part related to each of the ultrasound diagnosis apparatuses.

The plurality of pieces of information about the ultrasound diagnosis apparatuses may include information about whether each of the ultrasound diagnosis apparatuses communicates with another ultrasound probe.

The plurality of pieces of information about the ultrasound diagnosis apparatuses may include at least one of information about the other ultrasound probe that communicates with one of the ultrasound diagnosis apparatuses, information about a time when communication between the other ultrasound probe and one of the ultrasound diagnosis apparatuses ends, and usage reservation information of the other ultrasound probe with respect to one of the ultrasound diagnosis apparatuses.

When wireless communication between the ultrasound probe and the ultrasound diagnosis apparatus is discontinued, the method may further include an operation of providing information indicating that the wireless communication is discontinued.

When wireless communication between the ultrasound probe and the ultrasound diagnosis apparatus is discontinued, the method may further include an operation of transmitting the ultrasound image data to another ultrasound diagnosis apparatus.

When wireless communication between the ultrasound probe and the ultrasound diagnosis apparatus that can communicate with the ultrasound probe by using a plurality of wireless communication methods is discontinued, the method may further include an operation of transmitting the ultrasound image data to another ultrasound diagnosis apparatus by using another wireless communication method, instead of using the determined wireless communication method.

When a strap that is connected to the ultrasound probe is detached from the ultrasound probe, the operations of obtaining, displaying, and wireless transmitting may be performed.

According to another aspect of the present invention, there is provided an ultrasound probe including an information obtaining unit for obtaining a plurality of pieces of information about ultrasound diagnosis apparatuses; a display unit for displaying an ultrasound diagnosis apparatus list, based on the plurality of pieces of information about the ultrasound diagnosis apparatuses; a user input unit for receiving an input for selecting an ultrasound diagnosis apparatus from the ultrasound diagnosis apparatus list; a control unit for selecting the ultrasound diagnosis apparatus, based on the input; and a communication unit for wirelessly transmitting ultrasound image data to the ultrasound diagnosis apparatus, wherein the ultrasound image data is generated by the ultrasound probe.

The ultrasound diagnosis apparatus list may include information about a wireless communication method that can be used by the ultrasound probe to transmit the ultrasound image data to at least one of the ultrasound diagnosis apparatuses, the control unit may determine a wireless communication method that is used to transmit the ultrasound image data to the ultrasound diagnosis apparatus, and the communication unit may transmit the ultrasound image data to the ultrasound diagnosis apparatus by using the determined wireless communication method. Here, the determined wireless communication method may include at least one of wireless local area network (LAN), Wi-Fi, Bluetooth, ZigBee, Wi-Fi Direct (WFD), ultra wideband (UWB), infrared data association (IrDA), Bluetooth low energy (BLE), near field communication (NFC), wireless broadband internet (Wibro), world interoperability for microwave access (WiMAX), shared wireless access protocol (SWAP), and radio frequency (RF) communication.

The plurality of pieces of information about the ultrasound diagnosis apparatuses may include information about a diagnosis department or a diagnosis part related to each of the ultrasound diagnosis apparatuses.

The plurality of pieces of information about the ultrasound diagnosis apparatuses may include information about whether each of the ultrasound diagnosis apparatuses communicates with another ultrasound probe.

The plurality of pieces of information about the ultrasound diagnosis apparatuses may include at least one of information about the other ultrasound probe that communicates with one of the ultrasound diagnosis apparatuses, information about a time when communication between the other ultrasound probe and one of the ultrasound diagnosis apparatuses ends, and usage reservation information of the other ultrasound probe with respect to one of the ultrasound diagnosis apparatuses.

When wireless communication between the ultrasound probe and the ultrasound diagnosis apparatus is discontinued, the control unit may provide information indicating that the wireless communication is discontinued.

When wireless communication between the ultrasound probe and the ultrasound diagnosis apparatus is discontinued, the control unit may control the communication unit to transmit the ultrasound image data to another ultrasound diagnosis apparatus.

When wireless communication between the ultrasound probe and the ultrasound diagnosis apparatus that can communicate with the ultrasound probe by using a plurality of wireless communication methods is discontinued, the control unit may control the communication unit to transmit the ultrasound image data to another ultrasound diagnosis apparatus by using another wireless communication method, instead of using the determined wireless communication method.

When a strap that is connected to the ultrasound probe is detached from the ultrasound probe, the ultrasound probe may be activated.

According to another aspect of the present invention, there is provided a computer-readable recording medium having recorded thereon a program for executing the method, by using a computer.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, the present invention will be described in detail by explaining exemplary embodiments of the invention with reference to the attached drawings. The invention may, however, be embodied in many different forms, and should not be construed as being limited to the embodiments set forth herein; rather, these embodiments are provided so that this disclosure will be thorough and complete, and will fully convey the concept of the invention to those of ordinary skill in the art. In the following description, well-known functions or constructions are not described in detail since they would obscure the invention with unnecessary detail, and like reference numerals in the drawings denote like or similar elements throughout the specification.

Throughout the specification, it will also be understood that when an element is referred to as being "connected to" another element, it can be directly connected to the other element, or intervening elements may also be present. Also, when a part "includes" or "comprises" an element, unless there is a particular description contrary thereto, the part can further include other elements, not excluding the other elements.

Throughout the specification, a term 'target object' may be a target inanimate object or a target animate object, which is displayed via an image. Also, the target object may be a part of a human body and may include the liver, the heart, the womb, the brain, the breast, the abdominal region, or the like, a fetus, or a cross-section of a part of a human body. Throughout the specification, a "user" may be a medical expert including a doctor, a nurse, a medical laboratory technologist, a sonographer, or the like.

Hereinafter, the present invention will be described in detail by explaining exemplary embodiments of the invention with reference to the attached drawings.

Expressions such as "at least one of," when preceding a list of elements, modify the entire list of elements and do not modify the individual elements of the list.

Figure 1:
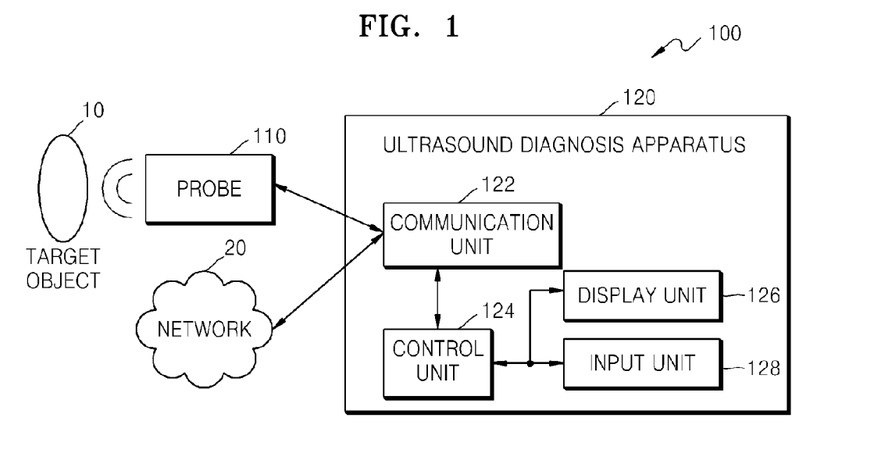
FIG. 1 is a block diagram of a general ultrasound system including a wireless ultrasound probe.

FIG. 1 is a block diagram of a general ultrasound system 100 including a wireless ultrasound probe 110.

The ultrasound system 100 may include the wireless ultrasound probe 110 and an ultrasound diagnosis apparatus 120.

The wireless ultrasound probe 110 may be wirelessly connected with the ultrasound diagnosis apparatus 120, so that the wireless ultrasound probe 110 may transmit an ultrasound signal to a target object according to a control signal that is transmitted from the ultrasound diagnosis apparatus 120 and may generate a reception signal by receiving an ultrasound signal (e.g., an ultrasound echo signal) that is reflected from the target object. The wireless ultrasound probe 110 may generate ultrasound image data by focusing the reception signal and then may transmit the ultrasound image data to the ultrasound diagnosis apparatus 120.

The ultrasound diagnosis apparatus 120 may be wirelessly connected with the wireless ultrasound probe 110, so that the ultrasound diagnosis apparatus 120 may generate an ultrasound image by using the ultrasound image data transmitted from the wireless ultrasound probe 110, and may display the ultrasound image. The ultrasound diagnosis apparatus 120 may include a communication unit 122, a control unit 124, a display unit 126, and an input unit 128.

The communication unit 122 may perform wireless communication with the wireless ultrasound probe 110. The communication unit 122 may transmit the control signal from the control unit 124 to the wireless ultrasound probe 110, and may receive the ultrasound image data that is transmitted from the wireless ultrasound probe 110.

Also, the communication unit 122 may be wired or wirelessly connected with a network 20, thereby communicating with an external device or a server. The communication unit 122 may exchange data with a hospital server or other medical apparatuses in a hospital via a picture archiving and communication system (PACS). Also, the communication unit 122 may perform data communication according to the digital imaging and communications in medicine (DICOM) standard.

The communication unit 122 may transmit or receive data such as an ultrasound image, ultrasound data, Doppler data, or the like of the target object, which are related to a diagnosis about the target object, and may transmit or receive a medical image captured by the other medical apparatuses such as a computerized tomography (CT) apparatus, a magnetic resonance imaging (MRI) apparatus, an X-ray apparatus, or the like. Furthermore, the communication unit 122 may receive information such as a diagnosis history or a treatment schedule about a patient from the hospital server, and then may use the information in the diagnosis about the target object. In addition, the communication unit 122 may perform data communication with not only the hospital server or the other medical apparatuses in the hospital but also may perform data communication with a portable terminal of a doctor or a customer.

The control unit 124 may generate a control signal so as to control an operation of the wireless ultrasound probe 110 according to user-requested information that is provided via the input unit 128. The control signal may include a control signal that is used to control the wireless ultrasound probe 110 to generate an ultrasound signal, and a control signal that is used to control transmission and reception of the ultrasound signal. In addition, the control unit 124 may control wireless communication with the wireless ultrasound probe 110, and may control generation and display of an ultrasound image.

According to the user-requested information via the input unit 128, the control unit 124 may perform various signal processing operations (e.g., gain adjustment or the like) on the ultrasound image data, which is transmitted from the wireless ultrasound probe 110) so as to generate the ultrasound image. The control unit 124 may generate the ultrasound image that corresponds to the user-requested information, by using a signal-processed reception signal.

The display unit 126 may display the ultrasound image, which is generated by the control unit 124, on a screen.

The input unit 128 is formed with a control panel, a mouse, a keyboard, or the like, and may generate the user-requested information in response to a user request. The user-requested information may include a selection about an application indicating a diagnosis part of the target object, a selection about a diagnosis mode at which the ultrasound image is generated, an adjustment of various gain values, or the like.

However, when a wireless ultrasound probe is subordinate to one ultrasound diagnosis apparatus, respective wireless ultrasound probes have to be arranged to correspond to respective ultrasound diagnosis apparatuses, and thus, it is expensive to arrange the wireless ultrasound probes and it is difficult to maintain the wireless ultrasound probes.

Thus, one or more embodiments of the present invention provide an ultrasound probe which is not subordinate a ultrasound diagnosis apparatus but capable of communicating with a plurality of ultrasound diagnosis apparatuses.

Also, one or more embodiments of the present invention provide an ultrasound probe capable of automatically or manually selecting a communication method that is the most appropriate for a usage environment, by selecting a wireless communication method with respect to an ultrasound diagnosis apparatus, and a communication method of the ultrasound probe.

Also, one or more embodiments of the present invention provide the ultrasound probe that displays an ultrasound diagnosis apparatus list, based on a plurality of pieces of information about ultrasound diagnosis apparatuses, so as to allow a user to rapidly and correctly recognize information when the user selects an ultrasound diagnosis apparatus, and a communication method of the ultrasound probe.

Figure 2:
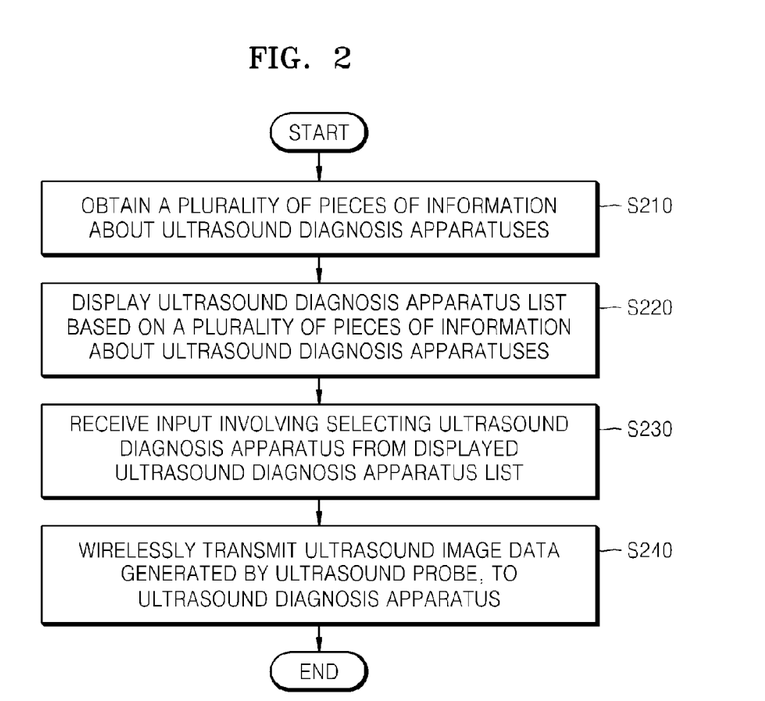
FIG. 2 is a flowchart of a communication method of an ultrasound probe, according to an embodiment of the present invention.

FIG. 2 is a flowchart of a communication method of the ultrasound probe 400 (refer to FIG. 4), according to an embodiment of the present invention.

In operation S210, the ultrasound probe 400 may obtain a plurality of pieces of information about ultrasound diagnosis apparatuses.

Here, the "ultrasound diagnosis apparatus" may mean an apparatus that is wirelessly connected with the ultrasound probe 400 and that provides ultrasound image data, which is transmitted from the ultrasound probe 400, to a user by processing the ultrasound image data. Also, the ultrasound diagnosis apparatus may generate an ultrasound image by using the ultrasound image data, which is transmitted from the ultrasound probe 400, and then may display the ultrasound image.

The "information about the ultrasound diagnosis apparatus" may include at least one of a name of the ultrasound diagnosis apparatus, function information about the ultrasound diagnosis apparatus, and status information about the ultrasound diagnosis apparatus.

The function information about the ultrasound diagnosis apparatus may include at least one of a wireless communication method that is provided by the ultrasound diagnosis apparatus, an application that is applied to the ultrasound diagnosis apparatus, a diagnosis department or a diagnosis part at which the ultrasound diagnosis apparatus is possibly used, and a class of the ultrasound diagnosis apparatus.

The "application" may include all types of application software which are used by the ultrasound diagnosis apparatus so as to process images. For example, the ultrasound diagnosis apparatus may use different applications according to diagnosis departments or diagnosis parts at which the ultrasound diagnosis apparatus is used. For example, the diagnosis departments may include an obstetrics (OB) department, a gynecology (GYN) department, a pediatrics (PD) department, a chest surgery (CS) department, a radiology (RD) department, a neurosurgery (NS) department, an abdomen department, or the like.

The class of the ultrasound diagnosis apparatus may be decided by a user or a manufacturer of the ultrasound diagnosis apparatus according to a quality of an ultrasound image or a total number of applications that the ultrasound diagnosis apparatus may provide.

Also, the status information about the ultrasound diagnosis apparatus may include at least one of whether the ultrasound diagnosis apparatus communicates with the ultrasound probe 400; information about the ultrasound probe 400 that communicates with the ultrasound diagnosis apparatus; a time when communication between the ultrasound diagnosis apparatus and the ultrasound probe 400 ends; usage reservation information of the ultrasound probe 400 with respect to the ultrasound diagnosis apparatus; a wireless communication strength of the ultrasound diagnosis apparatus; and a position of the ultrasound diagnosis apparatus.

For example, the information about the ultrasound diagnosis apparatus may include information about a wireless communication method by which the ultrasound probe 400 transmits ultrasound image data to the ultrasound diagnosis apparatus.

The wireless communication method that the ultrasound probe 400 uses may include, but is not limited to, wireless local area network (LAN), Wi-Fi, Bluetooth, ZigBee, Wi-Fi Direct (WFD), ultra wideband (UWB), infrared data association (IrDA), Bluetooth low energy (BLE), near field communication (NFC), wireless broadband internet (Wibro), world interoperability for microwave access (Wi-MAX), shared wireless access protocol (SWAP), and radio frequency (RF) communication.

The ultrasound probe 400 may receive data signals that are transmitted from the ultrasound diagnosis apparatuses and then may obtain the plurality of pieces of information about the ultrasound diagnosis apparatuses based on the data signals. Also, the ultrasound probe 400 may obtain the plurality of pieces of information about the ultrasound diagnosis apparatuses based on a user input, or may obtain previously stored information from a storage unit.

In operation S220, the ultrasound probe 400 may display the ultrasound diagnosis apparatus list based on the plurality of pieces of information about the ultrasound diagnosis apparatuses which are obtained in operation S210.

The ultrasound diagnosis apparatus list may display identifiers (e.g., names, allocated numbers, allocated letters, or allocated symbols of the ultrasound diagnosis apparatuses) that correspond to the ultrasound diagnosis apparatuses, and the plurality of pieces of information about the ultrasound diagnosis apparatuses which are obtained in operation S210.

For example, the ultrasound diagnosis apparatus list may include names of the ultrasound diagnosis apparatuses, and one or more wireless communication methods that can be used in communication between the ultrasound diagnosis apparatuses and the ultrasound probe 400.

In operation S230, the ultrasound probe 400 may receive an input involving selecting at least one ultrasound diagnosis apparatus from the ultrasound diagnosis apparatus list that is displayed in operation S220. For example, the input that involves selecting at least one ultrasound diagnosis apparatus may be a command that is input by the user or is previously stored in the storage unit 470.

The ultrasound probe 400 may recognize a user input involving selecting at least one ultrasound diagnosis apparatus from the displayed ultrasound diagnosis apparatus list.

For example, the user may input the command involving selecting at least one ultrasound diagnosis apparatus, via a user input unit that is included in the ultrasound probe 400.

In operation S240, the ultrasound probe 400 may wirelessly transmit ultrasound image data to the ultrasound diagnosis apparatus selected in operation S230. Here, the ultrasound probe 400 may determine a wireless communication method used by the ultrasound probe 400 to transmit the ultrasound image data to the ultrasound diagnosis apparatus, and may transmit the ultrasound image data to the ultrasound diagnosis apparatus by using the determined wireless communication method.

For example, the ultrasound probe 400 may receive a user input that selects the ultrasound diagnosis apparatus and the wireless communication method from the ultrasound diagnosis apparatus list that displays one or more wireless communication methods that can be used in the communication between the ultrasound diagnosis apparatuses and the ultrasound probe 400.

As described above, according to the present embodiment, the ultrasound probe 400 may automatically or manually select a communication method that is the most appropriate for a usage environment, by selecting the wireless communication method with respect to the ultrasound diagnosis apparatus. Here, the one or more wireless communication methods that the ultrasound probe 400 may use are not limited to the aforementioned examples.

Accordingly, the spirit and scope of the present invention may also include various changes in form and details which may be made by those of ordinary skill in the art, in view of a basic concept according to the present embodiment, e.g., a feature in which the ultrasound probe 400 may select at least one wireless communication method from among various wireless communication methods with respect to the ultrasound diagnosis apparatus. Also, it will be understood by those of ordinary skill in the art that the spirit and scope of the present invention may include any ultrasound probe that may communicate with the ultrasound diagnosis apparatuses by using not only the aforementioned wireless communication methods but also using other wireless communication methods similar to the aforementioned wireless communication methods, and that may select at least one wireless communication method from among the wireless communication methods.

In the ultrasound system 100 shown in FIG. 1, the ultrasound diagnosis apparatus 120 may be wirelessly connected with the wireless ultrasound probe 110, so that the ultrasound diagnosis apparatus 120 may generate the ultrasound image by using the ultrasound image data transmitted from the wireless ultrasound probe 110, and may display the ultrasound image. When the ultrasound diagnosis apparatus 120 provides the ultrasound image data for a diagnosis to a user in real-time, it is required for the wireless ultrasound probe 110 to seamlessly provide the ultrasound image data to the ultrasound diagnosis apparatus 120.

Thus, in order for the wireless ultrasound probe 110 to seamlessly provide the ultrasound image data to the ultrasound diagnosis apparatus 120, stable wireless communication between the wireless ultrasound probe 110 and the ultrasound diagnosis apparatus 120 is required.

According to the present embodiment, when wireless communication with the ultrasound diagnosis apparatus is discontinued, the ultrasound probe 400 capable of stably communicating with the ultrasound diagnosis apparatus may provide information indicating that the wireless communication with the ultrasound diagnosis apparatus is discontinued.

Thus, according to the information provided from the ultrasound probe 400, the user may input a command to the ultrasound probe 400, wherein the command controls the ultrasound probe 400 to transmit the ultrasound image data by using another wireless communication method. Alternatively, the user may input a command to the ultrasound probe 400, wherein the command controls the ultrasound probe 400 to transmit the ultrasound image data to another ultrasound diagnosis apparatus.

Also, in another embodiment, when the wireless communication with the ultrasound diagnosis apparatus is discontinued, the ultrasound probe 400 may automatically change a wireless communication method or a target ultrasound diagnosis apparatus to receive the ultrasound image data.

A detailed operating method of the ultrasound probe 400 capable of stably communicating with the ultrasound diagnosis apparatus will now be described with reference to FIG. 3.

Figure 3:
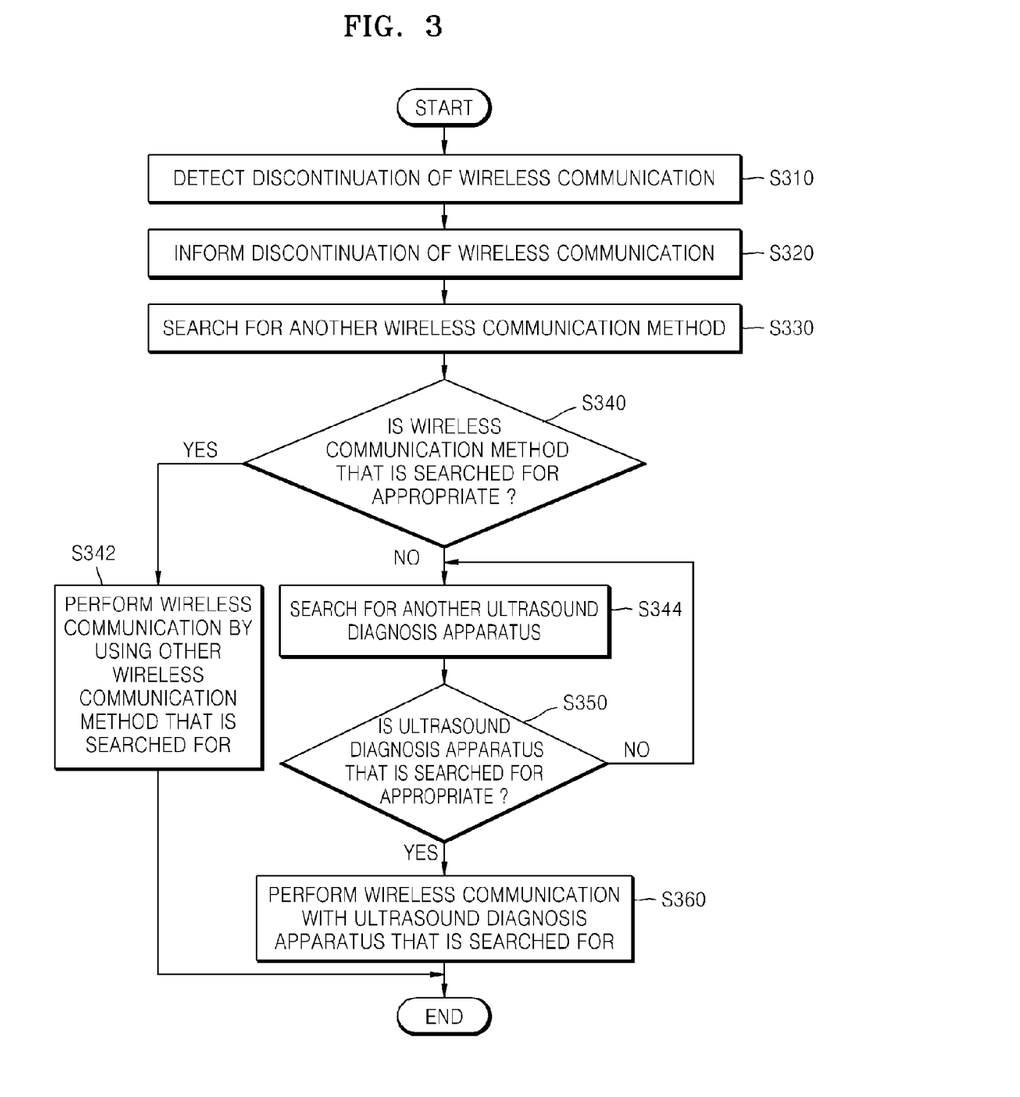
FIG. 3 is a flowchart of an operating method of the ultrasound probe when wireless communication with an ultrasound diagnosis apparatus is discontinued, according to an embodiment of the present invention.

FIG. 3 is a flowchart of an operating method of the ultrasound probe 400 when wireless communication with an ultrasound diagnosis apparatus is discontinued, according to an embodiment of the present invention.

In operation S310, the ultrasound probe 400 may detect that wireless communication with an ultrasound diagnosis apparatus selected in operation S230 of FIG. 2 is discontinued. The ultrasound probe 400 may periodically determine whether wireless communication is normally performed. Whether the wireless communication is normally performed may be determined in consideration of the strength of data signals that are transmitted and received. Alternatively, the ultrasound probe 400 may receive a data signal indicating the discontinuation of the wireless communication from the ultrasound diagnosis apparatus, so that the ultrasound probe 400 may detect the discontinuation of the wireless communication.

In operation S320, the ultrasound probe 400 may inform the user of the discontinuation of the wireless communication which is detected in operation S310. Information indicating the discontinuation of the wireless communication may be provided in a video or audio form.

In operation S330, the ultrasound probe 400 may search for another wireless communication method other than the wireless communication method of which wireless communication is discontinued. The ultrasound probe 400 may search for the other wireless communication method, based on a priority order of the stored wireless communication methods, wherein the other wireless communication is ranked as a next one of the wireless communication method of which wireless communication is discontinued, in the priority order. Here, the priority order of the stored wireless communication methods may be automatically determined based on a plurality of pieces of ultrasound diagnosis apparatus information such as distances between the ultrasound diagnosis apparatuses and ultrasound probe 400, or the like, or may be manually determined in response to a user input.

In operation S340, the ultrasound probe 400 may determine whether the other wireless communication method that is searched for in operation S330 is appropriate to perform wireless communication with the ultrasound diagnosis apparatus that is selected in operation S230. The ultrasound probe 400 may determine whether the other wireless communication method is appropriate, based on whether the ultrasound diagnosis apparatus that is selected in operation S230 supports the other wireless communication method, a distance between the ultrasound diagnosis apparatus and the ultrasound probe 400, and the strength of signals exchanged with the ultrasound diagnosis apparatus when the other wireless communication method is used.

If the other wireless communication method is appropriate to perform the wireless communication with the ultrasound diagnosis apparatus that is selected in operation S230, in operation S342, the ultrasound probe 400 may perform the wireless communication by using the other wireless communication method.

On the other hand, if the other wireless communication method is not appropriate to perform the wireless communication with the ultrasound diagnosis apparatus that is selected in operation S230, the ultrasound probe 400 may search for another wireless communication method.

According to the operating method of the ultrasound probe 400 shown in FIG. 3, in operation S344, when the other wireless communication method is not appropriate for the ultrasound probe 400 to perform wireless communication with the ultrasound diagnosis apparatus that is selected in operation S230, the ultrasound probe 400 may search for another ultrasound diagnosis apparatus to which the ultrasound probe 400 transmits the ultrasound image data.

In order to search for the other ultrasound diagnosis apparatus, the ultrasound probe 400 may perform again the operation of obtaining a plurality of pieces of information about ultrasound diagnosis apparatuses which is shown in operation S210 of FIG. 2. The ultrasound probe 400 may search for the other ultrasound diagnosis apparatus, based on the plurality of pieces of information about the ultrasound diagnosis apparatuses which are obtained again.

Alternatively, the ultrasound probe 400 may search for an ultrasound diagnosis apparatus as the other ultrasound diagnosis apparatus, based on a priority order of the stored ultrasound diagnosis apparatuses, wherein the ultrasound diagnosis apparatus is ranked as a next one of the ultrasound diagnosis apparatus that is selected in operation S230, in the priority order. Here, the priority order of the ultrasound diagnosis apparatuses may be automatically determined based on the plurality of pieces of obtained information about the ultrasound diagnosis apparatuses, or may be manually determined in response to a user input.

In operation S350, the ultrasound probe 400 may determine whether the other ultrasound diagnosis apparatus, which is searched for in operation S344, is appropriate to perform wireless communication with the ultrasound probe 400. For example, whether the other ultrasound diagnosis apparatus is appropriate to perform the wireless communication with the ultrasound probe 400 may be determined based on the strength of signals exchanged with the other ultrasound diagnosis apparatus or based on a user input.

For example, when the strength of the signals exchanged with the other ultrasound diagnosis apparatus is equal to or greater than a predetermined value, the ultrasound probe 400 may determine that the other ultrasound diagnosis apparatus is appropriate to perform the wireless communication with the ultrasound probe 400. A case in which the strength of the signals exchanged with the other ultrasound diagnosis apparatus is equal to or greater than the predetermined value may mean that a signal of ultrasound image data that is generated by the ultrasound probe 400 is sufficiently strong to be transmitted to the other ultrasound diagnosis apparatus.

When the other ultrasound diagnosis apparatus is not appropriate to perform the wireless communication with the ultrasound probe 400, the ultrasound probe 400 may return to operation S344 and then may search for another ultrasound diagnosis apparatus.

When the other ultrasound diagnosis apparatus is appropriate to perform the wireless communication with the ultrasound probe 400, in operation S360, the ultrasound probe 400 may perform the wireless communication with the other ultrasound diagnosis apparatus.

Figure 4:
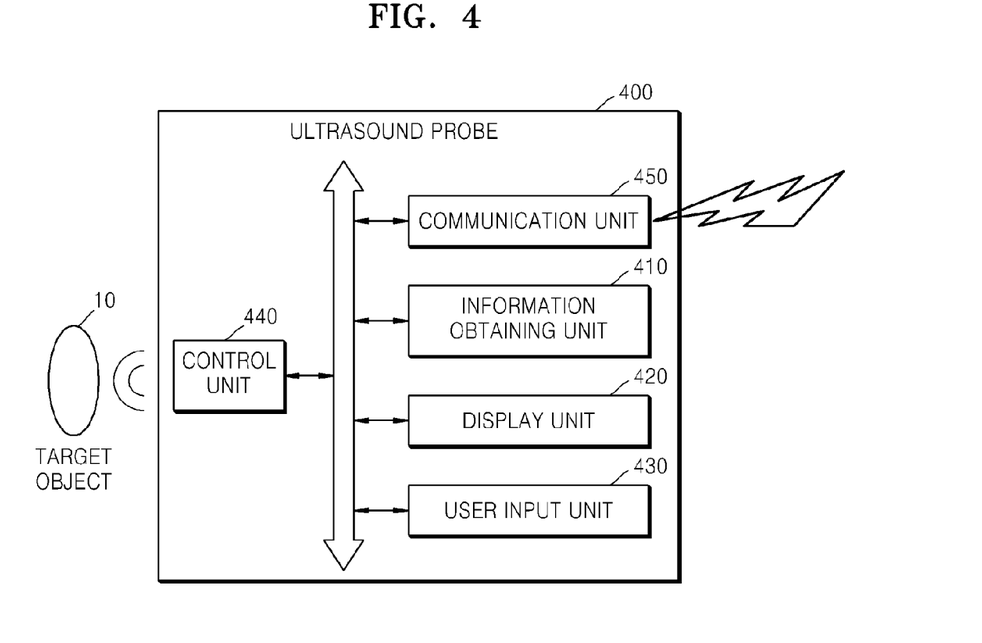
FIG. 4 is a block diagram of the ultrasound probe, according to an embodiment of the present invention.

FIG. 4 is a block diagram of the ultrasound probe 400, according to an embodiment of the present invention.

The ultrasound probe 400 may transmit an ultrasound signal to a target object, may receive an ultrasound signal (e.g., an ultrasound echo signal) that is reflected from the target object, and then may generate a reception signal. The ultrasound probe 400 may focus the reception signal, thereby generating ultrasound image data used in generation of an ultrasound image.

The ultrasound probe 400 may generate the ultrasound image data and then may transmit the generated ultrasound image data to an external device. Here, the "external device" that receives the generated ultrasound image data may include an ultrasound diagnosis apparatus, a display device, a personal computer (PC), a server, or the like.

Elements of the ultrasound probe 400 are configured to perform operations that constitute the communication method of the ultrasound probe 400 in FIG. 2. Thus, hereinafter, although descriptions may be omitted, if the descriptions are provided above with reference to the communication method of the ultrasound probe 400 in FIG. 2, the descriptions may also be applied to the ultrasound probe 400 shown in FIG. 4.

The ultrasound probe 400 may include an information obtaining unit 410, a display unit 420, the user input unit 430, a control unit 440, and a communication unit 450.

The information obtaining unit 410 may obtain a plurality of pieces of information about ultrasound diagnosis apparatuses. The information obtaining unit 410 may obtain the plurality of pieces of information about the ultrasound diagnosis apparatuses, based on data signals from the ultrasound diagnosis apparatuses or a user input.

The display unit 420 may display an ultrasound diagnosis apparatus list, based on the plurality of pieces of information about the ultrasound diagnosis apparatuses which are obtained by the information obtaining unit 410. The ultrasound diagnosis apparatus list may include the plurality of pieces of information about the ultrasound diagnosis apparatuses.

For example, the display unit 420 may display identifiers (e.g., names, allocated numbers, allocated letters, or allocated symbols of the ultrasound diagnosis apparatuses) that correspond to the ultrasound diagnosis apparatuses. Also, the display unit 420 may display wireless communication methods supported by the ultrasound diagnosis apparatuses, diagnosis departments or diagnosis parts related to the ultrasound diagnosis apparatuses, positions of the ultrasound diagnosis apparatuses, usage availability of the ultrasound diagnosis apparatuses, or the like.

Also, the display unit 420 may display state information related to an operation required to obtain ultrasound image data, a user interface (UI) or a graphic user interface (GUI) which is related to function setting, and an ultrasound image of the target object.

When a display panel of the display unit 420 and a touch pad to be described later form a mutual layer structure and thus are formed as a touch screen, the display unit 420 may be used as both an output device and an input device.

The display unit 420 may include at least one of a liquid crystal display (LCD), a thin film transistor-liquid crystal display (TFT-LCD), an organic light-emitting display device, a flexible display, a three-dimensional (3D) display, and an electrophoretic display.

The user input unit 430 may receive an input that involves selecting an ultrasound diagnosis apparatus from the ultrasound diagnosis apparatus list that is displayed on the display unit 420. The user input unit 430 may be formed of, but is not limited to, a key pad, a mouse, a dome switch, a touch pad (a touch capacitive type touch pad, a pressure resistive type touch pad, an infrared beam sensing type touch pad, a surface acoustic wave type touch pad, an integral strain gauge type touch pad, a piezoelectric effect type touch pad, or the like), a jog wheel, a jog switch, or the like. Also, the user input unit 430 may receive a user input which is transmitted from an external device that communicates with the ultrasound probe 400.

The control unit 440 controls all operations of the ultrasound probe 400, and controls the information obtaining unit 410, the display unit 420, the user input unit 430, and the communication unit 450 so as to perform wireless communication with the selected ultrasound diagnosis apparatus. The control unit 440 may select the ultrasound diagnosis apparatus based on the user input received by the user input unit 430.

The communication unit 450 may wirelessly transmit ultrasound image data to the selected ultrasound diagnosis apparatus. Also, the communication unit 450 may receive a control signal with respect to generation of the ultrasound image data from the ultrasound diagnosis apparatus. Also, the communication unit 450 may receive data signals including the plurality of pieces of information about the ultrasound diagnosis apparatuses, and then may output the data signals to the information obtaining unit 410.

Figure 5:
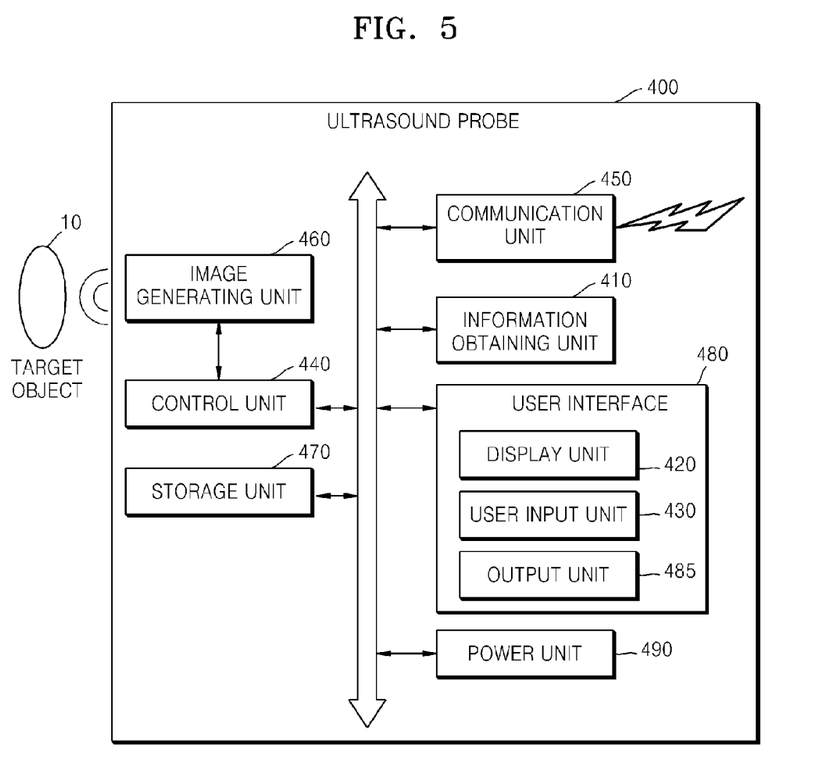
FIG. 5 is a block diagram of the ultrasound probe, according to another embodiment of the present invention.

FIG. 5 is a block diagram of the ultrasound probe 400, according to another embodiment of the present invention.

In the present embodiment, the ultrasound probe 400 may further include an image generating unit 460, the storage unit 470, a user interface 480, and a power unit 490.

The information obtaining unit 410, the display unit 420, the user input unit 430, the control unit 440, and the power unit 450 of the ultrasound probe 400 which are shown in FIG. 5 correspond to those of FIG. 4, thus, corresponding descriptions will be omitted here.

The image generating unit 460 may transmit an ultrasound signal to a target object and may generate a reception signal by receiving an ultrasound signal (e.g., an ultrasound echo signal) that is reflected from the target object.

The storage unit 470 stores various types of information required by the ultrasound probe 400 to operate. For example, the storage unit 470 may store, but is not limited to, the ultrasound signal that is transmitted from the image generating unit 460, the ultrasound echo signal, ultrasound image data that is generated from the ultrasound echo signal, the plurality of pieces of information about the ultrasound diagnosis apparatuses which are obtained by the information obtaining unit 410, or a control signal that is transmitted from one of the ultrasound diagnosis apparatuses.

The user interface 480 provides information related to operations of the ultrasound probe 400 to a user, and receives various types of an input for controlling the ultrasound probe 400 from the user. The user interface 480 may provide the information to the user by displaying a GUI related to function setting for the ultrasound probe 400 or by reproducing audio data, and may display an ultrasound image that is formed based on the reception signal formed by the image generating unit 460.

The user interface 480 may include the display unit 420 and the user input unit 430, and may further include an output unit 485. The output unit 485 that is different from the display unit 420 functions to inform the user about a mechanical error such as discontinuation of reception of a wireless power, and for example, the output unit 485 may include a light-emitting diode (LED), or the like.

The power unit 490 may receive a wireless power from an external source and may supply the wireless power to the ultrasound probe 400, or may supply a power that is charged in a battery (not shown) to the ultrasound probe 400. The battery may be charged by a power that is received wirelessly or by wire from an external source. The power unit 490 may supply the charged power to each of elements included in the ultrasound probe 400, in response to a control signal from the control unit 440.

Figure 6:
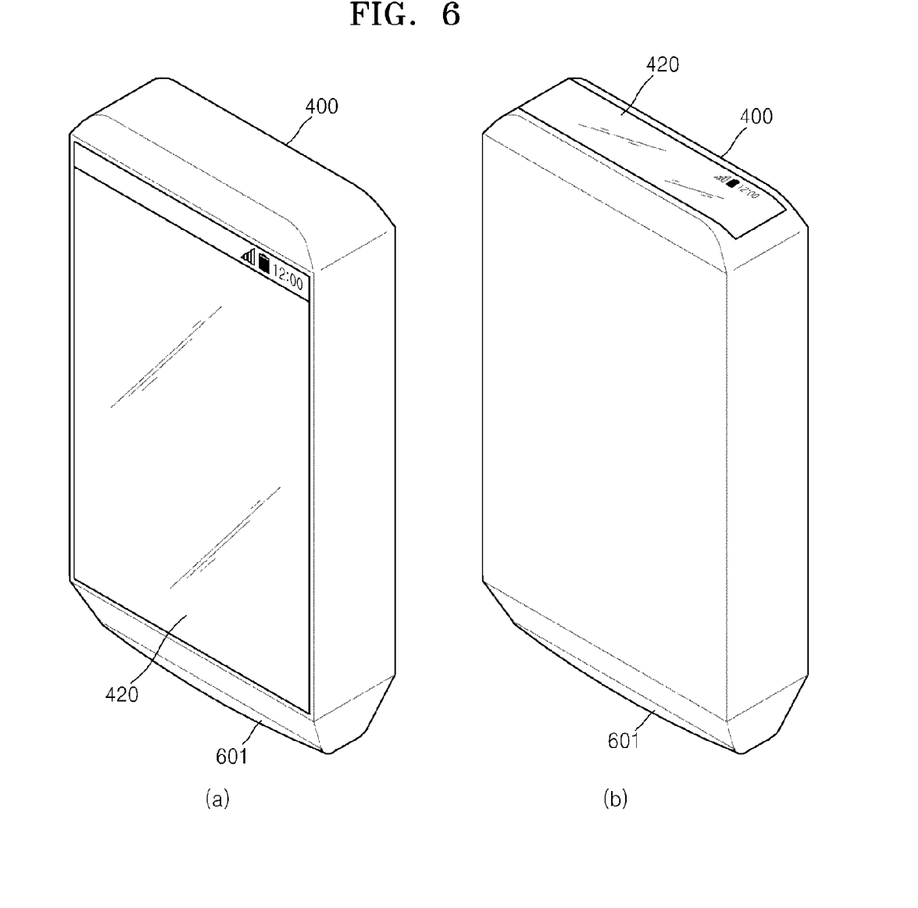
FIG. 6 is a diagram illustrating the ultrasound probe, according to an embodiment of the present invention.

FIG. 6 is a diagram illustrating the ultrasound probe 400, according to an embodiment of the present invention.

As illustrated in FIG. 6(a), the display unit 420 may be disposed at a side surface of the ultrasound probe 400 with respect to a bottom surface 601 of the ultrasound probe 400, wherein a transducer for receiving an ultrasound signal about a target object is disposed at the bottom surface 601.

Also, as illustrated in FIG. 6(b), the display unit 420 may be disposed at a top surface of the ultrasound probe 400. When the display unit 420 is disposed at the top surface, although a user scans a target object while the user holds the side surface of the ultrasound probe 400, a user's hand does not obstruct the display unit 420 so that readability of information that is provided by the ultrasound probe 400 is increased.

The display unit 420 may display the strength of signals exchanged with an ultrasound diagnosis apparatus, in the form of a text or an image. Also, the display unit 420 may display a state of a power charged in the battery. For example, the display unit 420 may display whether the battery is being charged, whether the battery needs to be charged, a remaining quantity of power, or the like, in the form of a text or an image.

Figure 7:
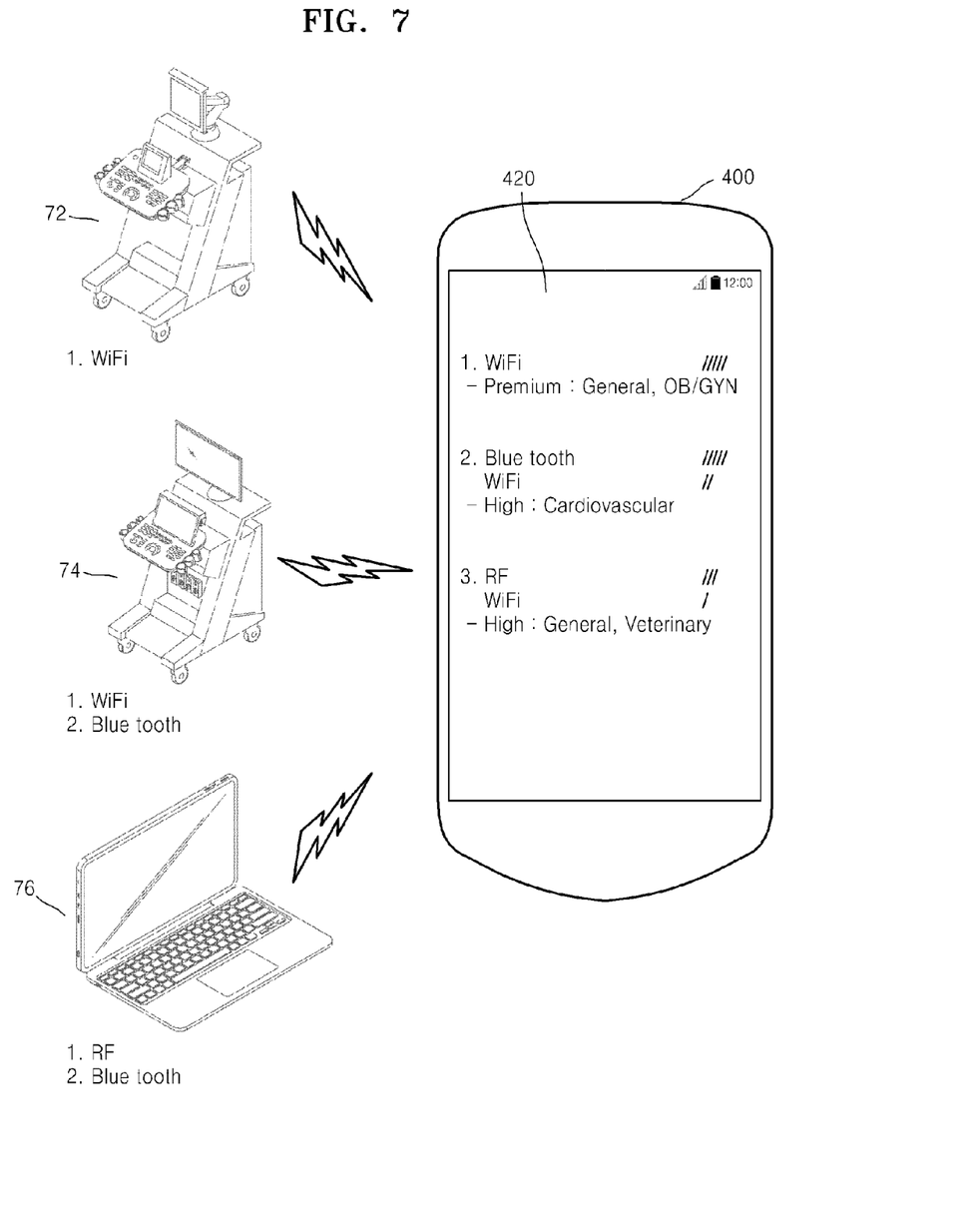
FIG. 7 illustrates a screen that is displayed on the ultrasound probe, according to an embodiment of the present invention.

FIG. 7 illustrates a screen that is displayed on the ultrasound probe 400, according to an embodiment of the present invention.

FIG. 7 illustrates the ultrasound probe 400, and a plurality of ultrasound diagnosis apparatuses 72, 74, and 76 capable of wirelessly communicating with the ultrasound probe 400.

As illustrated in FIG. 7, the ultrasound probe 400 may display an ultrasound diagnosis apparatus list on the display unit 420, according to a plurality of pieces of obtained information about the ultrasound diagnosis apparatuses 72, 74, and 76.

The ultrasound diagnosis apparatus list that is displayed on the display unit 420 includes wireless communication methods supported by the ultrasound diagnosis apparatuses 72, 74, and 76, classes of the ultrasound diagnosis apparatuses 72, 74, and 76, and diagnosis departments for which the ultrasound diagnosis apparatuses 72, 74, and 76 may be used.

For example, referring to the ultrasound diagnosis apparatus list illustrated in FIG. 7, the ultrasound diagnosis apparatus 72 may wirelessly communicate with the ultrasound probe 400 by using Wi-Fi, a class of the ultrasound diagnosis apparatus 72 may be "Premium", the ultrasound diagnosis apparatus 72 may be used for a general ultrasound diagnosis and for OB/GYN departments.

Also, the ultrasound diagnosis apparatus 74 may wirelessly communicate with the ultrasound probe 400 by using Bluetooth or Wi-Fi, a class of the ultrasound diagnosis apparatus 74 may be "High", and the ultrasound diagnosis apparatus 74 may be used for cardiovascular diagnosis.

The ultrasound probe 400 may express whether the ultrasound diagnosis apparatuses 72, 74, and 76 are appropriate to wirelessly communicate with the ultrasound probe 400, in the form of a figure, a text, or a color. For example, the ultrasound probe 400 shown in FIG. 7 expresses the strength of a signal transmitted from each of the ultrasound diagnosis apparatuses 72, 74, and 76, by using a number of bars.

Figure 8:
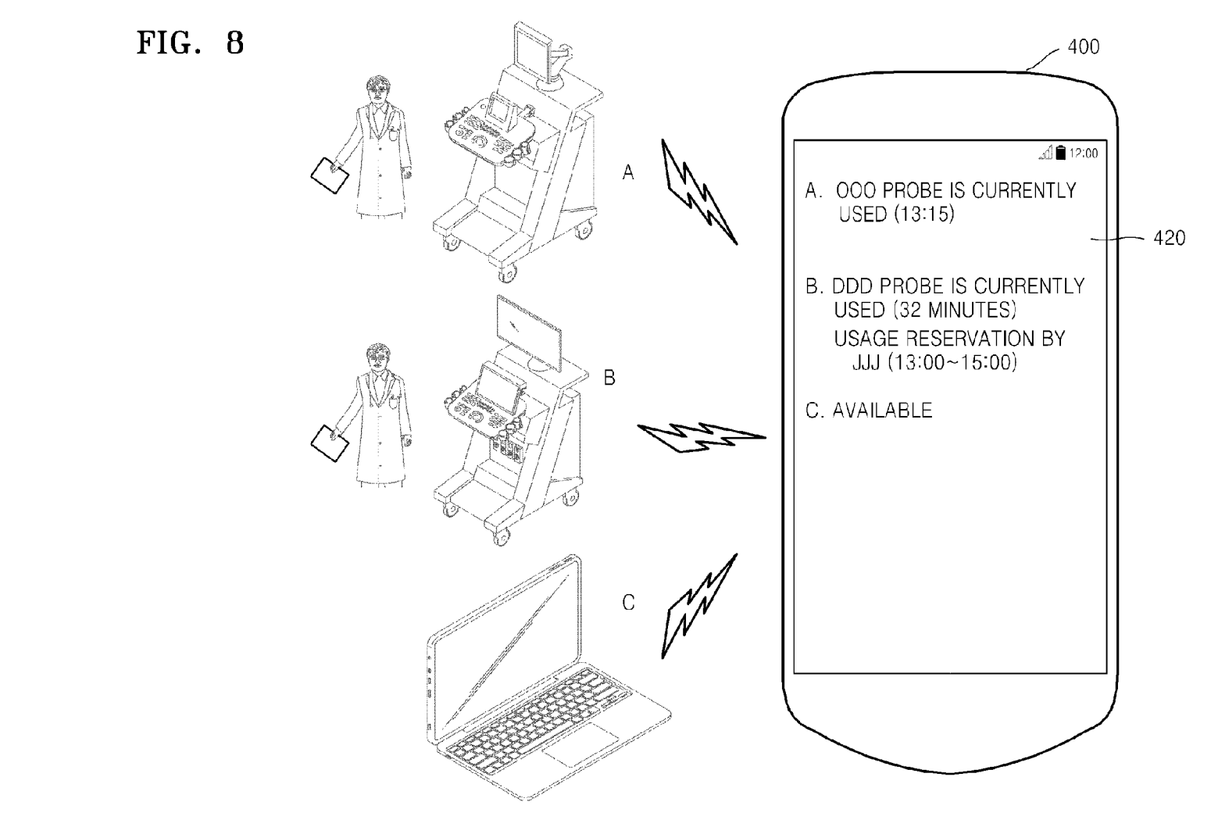
FIG. 8 illustrates a screen that is displayed on the ultrasound probe, according to another embodiment of the present invention.

FIG. 8 illustrates a screen that is displayed on the ultrasound probe 400, according to another embodiment of the present invention.

As illustrated in FIG. 8, the ultrasound probe 400 may display an ultrasound diagnosis apparatus list including a plurality of pieces of information about ultrasound diagnosis apparatuses A, B, and C.

Referring to FIG. 8, the plurality of pieces of information about the ultrasound diagnosis apparatuses A, B, and C may include at least one of whether any one of the ultrasound diagnosis apparatuses A, B, and C communicates with another ultrasound probe, information about an ultrasound probe that communicates with any one of the ultrasound diagnosis apparatuses A, B, and C, a time when communication between an ultrasound probe and any one of the ultrasound diagnosis apparatuses A, B, and C ends, and usage reservation information of an ultrasound probe with respect to one of the ultrasound diagnosis apparatuses A, B, and C.

The display unit 420 of the ultrasound probe 400 shown in FIG. 8 displays information indicating that the ultrasound diagnosis apparatus A is currently used by an OOO probe, and its usage will be finished at 13:15 p.m. Also, the display unit 420 displays information indicating that the ultrasound diagnosis apparatus B is currently used by a DDD probe, and its usage will be finished in 32 minutes. Also, referring to FIG. 8, it is possible to recognize that the ultrasound diagnosis apparatus B is reserved for use from 13:00 to 15:00 p.m. by a probe or user called JJJ.

Thus, a user who uses the ultrasound probe 400 shown in FIG. 8 selects the ultrasound diagnosis apparatus C that is currently available.

The time when communication between an ultrasound probe and any one of the ultrasound diagnosis apparatuses A, B, and C ends, and the usage reservation information of the ultrasound probe with respect to one of the ultrasound diagnosis apparatuses A, B, and C may be input via the ultrasound probe or a server by a user of the ultrasound probe.

Figure 9:
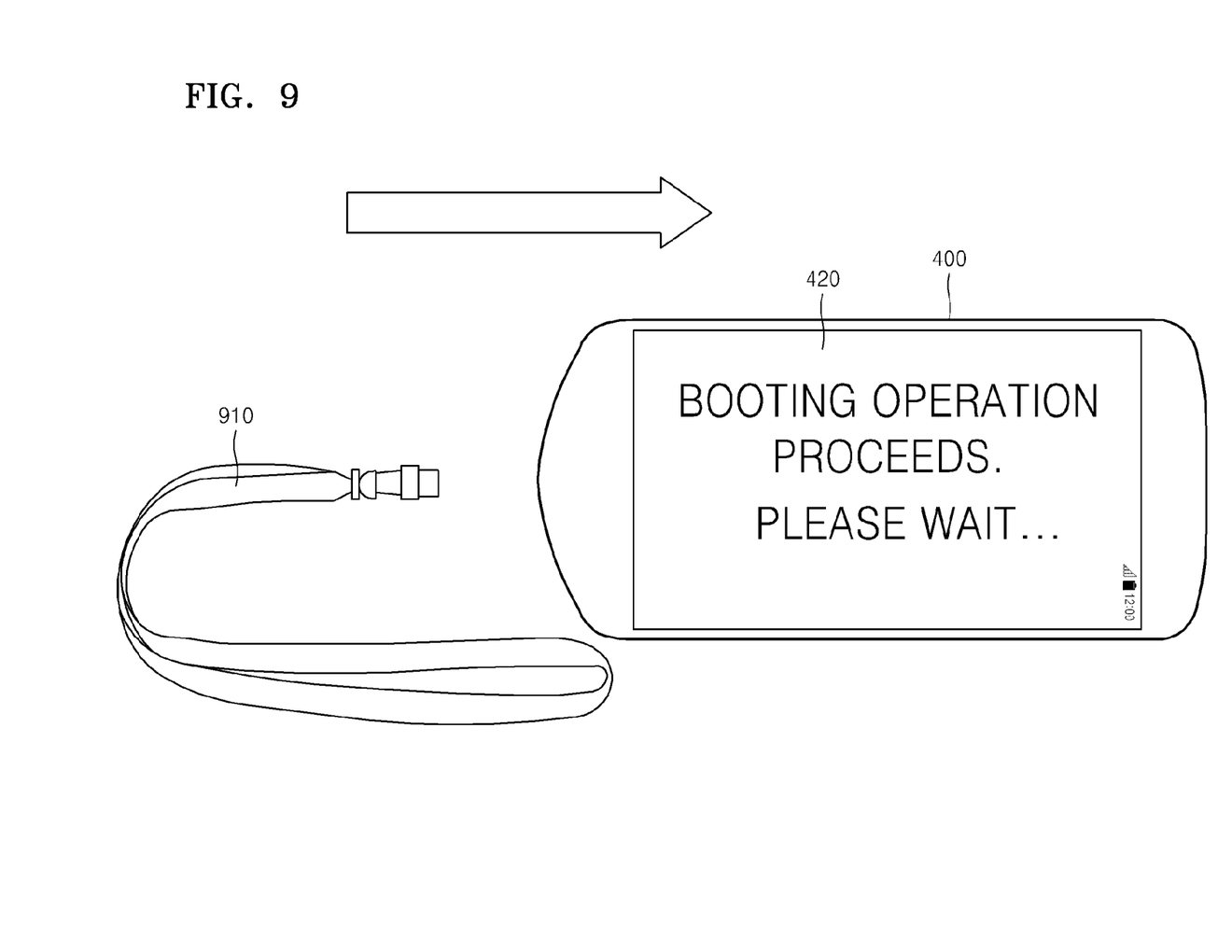
FIG. 9 illustrates a screen that is displayed on the ultrasound probe when a strap connected to the ultrasound probe is detached from the ultrasound probe, according to an embodiment of the present invention.

FIG. 9 illustrates a screen that is displayed on the ultrasound probe 400 when a strap 910 connected to the ultrasound probe 400 is detached from the ultrasound probe 400, according to an embodiment of the present invention.

As illustrated in FIG. 9, the strap 910 may be attached to the ultrasound probe 400. A user may conveniently carry the ultrasound probe 400 by using the strap 910.

When the user does not use the ultrasound probe 400, the user may keep the ultrasound probe 400 while the strap 910 is connected thereto, and when the user uses the ultrasound probe 400, the user may activate the ultrasound probe 400 by detaching the ultrasound probe 400 from the strap 910.

The activated ultrasound probe 400 may perform the communication method of the ultrasound probe 400 shown in FIG. 2. According to the embodiment of FIG. 9, it is convenient since the user can activate the ultrasound probe 400 without performing a separate operation such as an operation of pressing a button.

Figure 10:
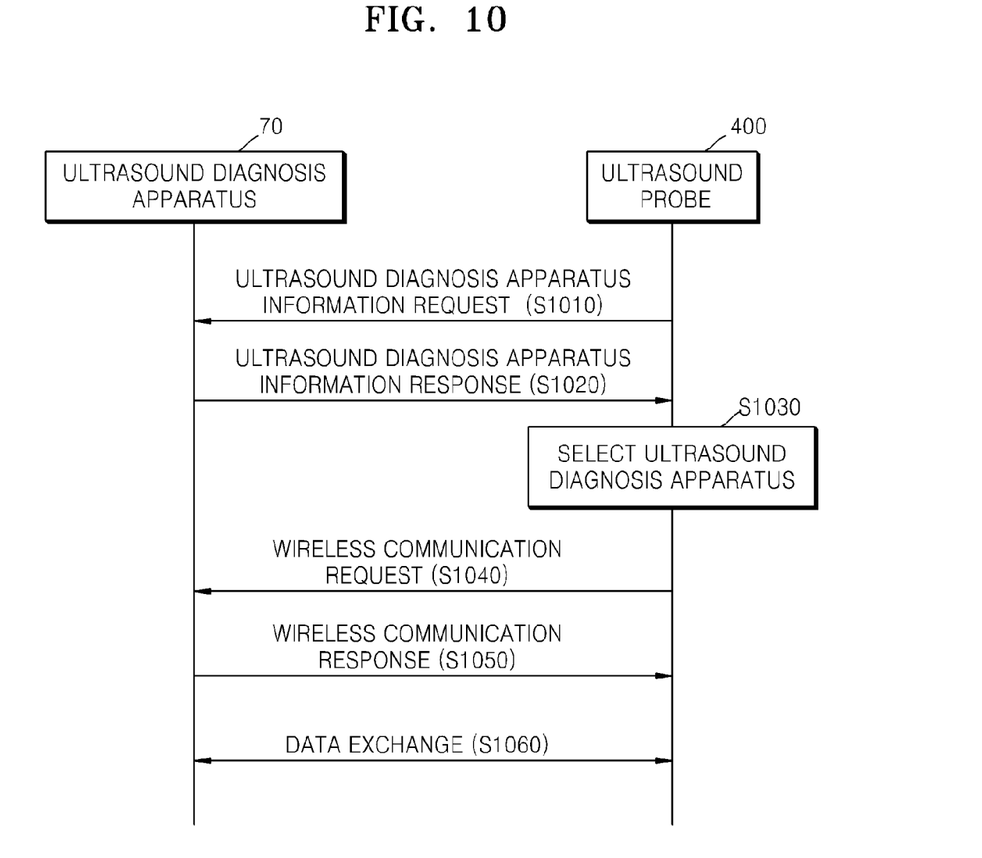
FIG. 10 is a signal flowchart of a procedure in which the ultrasound probe selects an ultrasound diagnosis apparatus and performs wireless communication, according to an embodiment of the present invention.

FIG. 10 is a signal flowchart of a procedure in which the ultrasound probe 400 selects an ultrasound diagnosis apparatus 70 and performs wireless communication, according to an embodiment of the present invention. In order for the ultrasound probe 400 to select the ultrasound diagnosis apparatus 70 and to perform the wireless communication, a general data communication method may be used.

In operation S1010, the ultrasound probe 400 may request information about the ultrasound diagnosis apparatus 70. The requested information about the ultrasound diagnosis apparatus 70 may include at least one of an identifier of the ultrasound diagnosis apparatus 70, a network address of the ultrasound diagnosis apparatus 70, and a wireless communication method that is supported by the ultrasound diagnosis apparatus 70.

In operation S1020, the ultrasound diagnosis apparatus 70 may transmit the information about the ultrasound diagnosis apparatus 70, in response to the request from the ultrasound probe 400.

In operation S1030, the ultrasound probe 400 may select the ultrasound diagnosis apparatus 70 and may determine to perform wireless communication with the ultrasound diagnosis apparatus 70, based on the received information about the ultrasound diagnosis apparatus 70.

In operation S1040, the ultrasound probe 400 may request the wireless communication to the ultrasound diagnosis apparatus 70. Here, the wireless communication request from the ultrasound probe 400 may include information about a protocol or synchronization related to performing the wireless communication.

In operation S1050, the ultrasound probe 400 may receive a response from the ultrasound diagnosis apparatus 70, wherein the response corresponds to the wireless communication request from the ultrasound probe 400. Here, the response from the ultrasound diagnosis apparatus 70 may include information about a protocol or synchronization related to performing the wireless communication.

In operation S1060, the ultrasound probe 400 may exchange data with the ultrasound diagnosis apparatus 70 that is selected in operation S1030.

According to the one or more embodiments of the present invention, the ultrasound probe is not subordinate to one ultrasound diagnosis apparatus but communicates with various ultrasound diagnosis apparatuses, whereby usability of the ultrasound probe may be increased.

Also, according to the one or more embodiments of the present invention, the ultrasound probe may allow a user to rapidly and correctly recognize user-required information by displaying the ultrasound diagnosis apparatus list based on the plurality of pieces of information about the ultrasound diagnosis apparatuses.

The one or more embodiments of the present invention may be embodied as a recording medium, e.g., a program module to be executed in computers, which include computer-readable commands. The computer storage medium may include any usable medium that may be accessed by computers, volatile and non-volatile medium, and detachable and non-detachable medium. Also, the computer storage medium may include a computer storage medium and a communication medium. The computer storage medium includes all of volatile and non-volatile medium, and detachable and non-detachable medium which are designed to store information including computer readable commands, data structures, program modules or other data. The communication medium includes computer-readable commands, a data structure, a program module, and other transmission mechanism, and includes other information transmission mediums.

The present invention may, however, be embodied in many different forms and should not be construed as being limited to the embodiments set forth herein; rather, these embodiments are provided so that this disclosure will be thorough and complete, and will fully convey the inventive concept to those of ordinary skill in the art. For example, configuring elements that are singular forms may be executed in a distributed fashion, and also, configuring elements that are distributed may be combined and then executed.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An ultrasound probe comprising:
    a processor for obtaining a plurality of pieces of information about ultrasound diagnosis apparatuses; and
    a display for displaying an ultrasound diagnosis apparatus list, based on the plurality of pieces of information about the ultrasound diagnosis apparatuses,
    wherein the processor receives an input for selecting an ultrasound diagnosis apparatus from the ultrasound diagnosis apparatus list, selects the ultrasound diagnosis apparatus, based on the input, and wirelessly transmits ultrasound image data to the selected ultrasound diagnosis apparatus,
    wherein the ultrasound image data is generated by the ultrasound probe, wherein the ultrasound diagnosis apparatus list comprises information about at least one wireless communication method that can be used by the ultrasound probe to transmit the ultrasound image data to at least one of the ultrasound diagnosis apparatuses, and wherein the processor determines a wireless communication method from among the at least one wireless communication method and transmits the ultrasound image data to the ultrasound diagnosis apparatus by using the determined wireless communication method.

2. The ultrasound probe of claim 1, wherein the determined wireless communication method comprises at least one of wireless local area network (LAN), Wi-Fi, Bluetooth, ZigBee, Wi-Fi Direct (WFD), ultra wideband (UWB), infrared data association (IrDA), Bluetooth low energy (BLE), near field communication (NFC), wireless broadband internet (Wibro), world interoperability for microwave access (WiMAX), shared wireless access protocol (SWAP), and radio frequency (RF) communication.

3. The ultrasound probe of claim 1, wherein the plurality of pieces of information about the ultrasound diagnosis apparatuses comprise information about a diagnosis department or a diagnosis part related to each of the ultrasound diagnosis apparatuses.

4. The ultrasound probe of claim 1, wherein the plurality of pieces of information about the ultrasound diagnosis apparatuses comprise information about whether each of the ultrasound diagnosis apparatuses communicates with another ultrasound probe.

5. The ultrasound probe of claim 4, wherein the plurality of pieces of information about the ultrasound diagnosis apparatuses comprise at least one of information about the other ultrasound probe that communicates with one of the ultrasound diagnosis apparatuses, information about a time when communication between the other ultrasound probe and one of the ultrasound diagnosis apparatuses ends, and usage reservation information of the other ultrasound probe with respect to one of the ultrasound diagnosis apparatuses.

6. The ultrasound probe of claim 1, wherein, when wireless communication between the ultrasound probe and the ultrasound diagnosis apparatus is discontinued, the processor provides information indicating that the wireless communication is discontinued.

7. The ultrasound probe of claim 1, wherein, when wireless communication between the ultrasound probe and the ultrasound diagnosis apparatus is discontinued, the processor transmits the ultrasound image data to another ultrasound diagnosis apparatus.

8. The ultrasound probe of claim 1, wherein, when wireless communication between the ultrasound probe and the ultrasound diagnosis apparatus that can communicate with the ultrasound probe by using a plurality of wireless communication methods is discontinued, the processor transmits the ultrasound image data to another ultrasound diagnosis apparatus by using another wireless communication method, instead of using the determined wireless communication method.

9. The ultrasound probe of claim 1, further comprising:
a strap configured to be detachably connected to the ultrasound probe,
wherein, when the strap that is connected to the ultrasound probe is detached from the ultrasound probe, the ultrasound probe is activated.

* * * * *